United States Patent [19]

Murakami et al.

[11] 4,092,428
[45] May 30, 1978

[54] PROCESS OF PREPARING STABLE PROSTAGLANDIN E GROUP-CONTAINING FORMULATION

[75] Inventors: Masuo Murakami, Higashikurume; Shigemi Kawahara, Tokyo; Hiroitsu Kawata; Kiyoshi Okazaki, both of Kawagoe; Jun Sekino, Kashiwa; Hidemi Shimizu, Ageo, all of Japan

[73] Assignee: Yamanouchi Pharmaceutical Co., Ltd., Tokyo, Japan

[21] Appl. No.: 774,680

[22] Filed: Mar. 7, 1977

Related U.S. Application Data

[62] Division of Ser. No. 516,217, Oct. 21, 1974, Pat. No. 4,036,954.

[30] Foreign Application Priority Data

Nov. 2, 1973 Japan .................................. 48-123669
June 25, 1974 Japan .................................. 49-72585

[51] Int. Cl.$^2$ ................... A61K 31/19; A61K 31/215
[52] U.S. Cl. ..................................... 424/317; 424/305
[58] Field of Search ................................ 424/305, 317

[56] References Cited

U.S. PATENT DOCUMENTS

| 3,826,823 | 7/1974 | O'Rourke et al. ................... 424/305 |
| 3,954,787 | 5/1976 | Monkhouse et al. ................ 424/305 |

*Primary Examiner*—Sam Rosen
*Attorney, Agent, or Firm*—Burgess, Ryan and Wayne

[57] ABSTRACT

There is provided a process of preparing a prostaglandin E group-containing formulation by adding to a prostaglandin E group at least one additive selected from the group consisting of thiol compound, a water-soluble high molecular weight compound, and a water-soluble salt of deoxycholic acid and then subjecting the mixture to lyophilization.

11 Claims, No Drawings

PROCESS OF PREPARING STABLE PROSTAGLANDIN E GROUP-CONTAINING FORMULATION

The parent application Ser. No. 516,217 was passed to issue on July 19, 1977, as U.S. Pat. No. 4,036,954, of which this application is a division.

BACKGROUND OF THE INVENTION

1. Field of the Invention

The present invention relates to a process of preparing a stable prostaglandin E group-containing formulation and more particularly it relates to a process of preparing a prostaglandin E group-containing formulation by adding to a prostaglandin group E at least one additive selected from the group consisting of a thiol compound, a water-soluble high molecular weight compound and a water-soluble salt of deoxycholic acid and subjecting the mixture to lyophilization.

In the invention, the term "prostaglandin E group" means prostaglandin $E_1$ represented by the formula

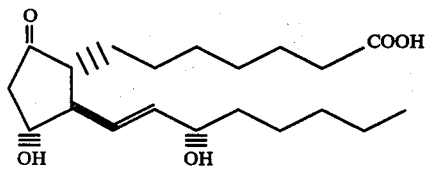

prostaglandin $E_2$ represented by the formula

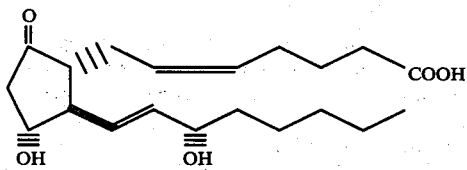

prostaglandin $E_3$ represented by the formula

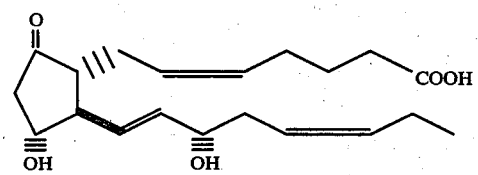

and the derivatives of these compound at the side chains, such as, for example, 16-methyl-prostaglandin $E_2$, 3-methyl-prostaglandin $E_2$, 3,16(R)-dimethyl-prostaglandin $E_2$, 17-oxo-15-epi-prostaglandin $E_2$, 16(R)-hydroxy-prostaglandin $E_2$, etc.

2. Description of the Prior Art

Prostaglandin E group is a medicament showing, even in a small amount, such medical actions as the control of the contractive force of the uterus, a hypotensive effect, treatment and prophylaxis of digestive organ ulcers, control of lipid metabolism, bronchodilator action, etc. However, since the compound is very unstable and is liable to be decomposed; that is, the compound is easily decomposed in not only a solution state but also in a crystalline state, it is ordinarily stored as the crystal thereof or an ethanol solution thereof in a refrigerator at $-20°$ C.

For stabilizing the prostaglandin E group, a process has hitherto been known in which the compound is dissolved in an organic solvent such as N,N-dimethylacetamide containing less than 0.1% water as disclosed in Belgian Pat. No. 790,840.

However, in the case of administering a medicament directly to the human body, in particular, administering by injection, the medicament may sometimes be administered in the form of an organic solution or in the form of an organic solution diluted with water but it is usually preferred to adminnister the medicament in the form of an aqueous solution (see, e.g., "Dispensing of Medication", 976(1971), 7th Ed., Mack Publishing Company).

Consequently, a stable prostaglandin E group-containing formulation is one which can store prostaglandin E group in a stable form and can be administered as an aqueous solution when administering by injection is desirable.

SUMMARY OF THE INVENTION

As the result of various investigations, the inventors have discovered that the prostanglandin E group-containing formulation prepared by adding to prostaglandin group E at least one additive selected from the group consisting of a thiol compound, a water-soluble high molecular weight compound and a water-soluble salt of deoxycholic acid and subjecting the mixture to lyophilization or freeze-drying can be stored for a long period of time at room temperature without being decomposed and can be administered as an aqueous solution and can be administered by injection.

That is, according to the present invention there is provided a process of preparing a stable prostaglandin E group-containing formulation which comprises adding to prostaglandin E group at least one additive selected from the group consisting of a thiol compound, a water-soluble high molecular weight compound and a water-soluble salt of deoxycholic acid and subjecting the mixture to lyophilization.

DETAILED DESCRIPTION OF THE INVENTION

Now, as described above, thiol compounds, water-soluble high molecular weight compounds and/or water-soluble salts of deoxycholic acid are used as additives in this invention and examples of the thiol compound are glutathione, cysteine, acetylcysteine, etc.; examples of water-soluble high molecular weight compounds are such natural or synthetic water-soluble polymers as dextran, gelatin, polyvinyl pyrrolidone, methyl cellulose, hydroxypropyl cellulose, hydroxyethyl cellulose, carboxymethyl cellulose, etc.; and examples of water-soluble salts of deoxycholic acid are the arginine salt, lysine salt, alkali metal salt, etc., of the acid.

In accordance with the process of this invention, water and at least one additive selected from the group consisting of a thiol compound, a water-soluble high molecular weight compound, and a water-soluble salt of deoxycholic acid are added to a prostaglandin E group to form an aqueous solution, after controlling the pH of the solution and then following a conventional operation such as sterile filtration, the solution is poured in ampoules or vials and then the solution is subjected to lyophilization by a conventional procedure. Furthermore, as the case may be, ordinary excipients such as saccharides, aminoacids, inorganic salts, etc., may be added to the aforesaid composition. When the water-soluble salt of deoxycholic acid is used, deoxycholic acid and a base capable of forming a water-soluble salt with the acid may be added to the aqueous solution to form the salt in the solution.

In addition, the prostaglandin E group is soluble in water but it takes a long period of time to dissolve the crystals thereof in water and hence when the crystals of prostaglandin E group are used, it is preferred that the crystals are at first dissolved in an organic solvent such as ethanol, ethyl acetate, etc., and then the organic solvent is distilled off to provide an amorphous solid so that the contact area thereof with water is enlarged.

The preferred amount of the additive used in this invention per a container is 1-20 mg. for the thiol compound, 5-150 mg. for the high molecular weight compound, in particular 0.1-150 mg. for the cellulose derivative among the high molecular weight compounds, and 5-100 mg. for the water-soluble salt of deoxycholic acid.

Moreover, if necessary, such additives as an isotonic agent, an antiseptic, an excipient, an analgesic, etc., may be added to the stable composition containing the prostaglandin E group.

The following experiment shows that the prostaglandin E group-containing formulation obtained by the process of this invention can be stably stored for a long period of time.

EXPERIMENT

After adding 1 ml. of water per ampoule to each of the lyophilized products obtained in Examples 2-6, 2 ml. of water to the lyophilized product obtained in Example 1, and 1 ml. of water per vial to the lyophilized products obtained in Examples 7-15 to dissolve the product in water in each case and adjusting each solution to pH ≦ 3 with citric acid, the product was extracted with ethyl acetate, preferably with ice cooling. The extract was dried and concentrated. In addition, when 1 ml. of water per ampoule was added to each of the lyophilized products obtained in Examples 5 and 6 to dissolve the product and the solution was adjusted to pH ≦ 3 with cirtic acid, deoxycholic acid precipitated and thus the product was extracted with ethyl acetate after filtering off the precipitates and then the extract was dried and concentrated. Then, the whole amount of the concentrate was applied to a silica gel thin layer chromatography and the adsorbate was developed with a mixture of chloroform, methanol, acetic acid and water of 90 : 8 : 1 : 0.8 by volume ratio (when the lyophilized products obtained in Examples 5 and 6 were used, the adsorbate was developed with a mixture of ethyl acetate, acetic acid, isooctane, and water of 90 : 20 : 50 : 100 by volume ratio). Then, an ethanol solution of 5% phosphomolybdic acid was sprayed over the developed product followed by heating for 10 minutes at 105°-110° C. to develop coloring, the absorbance of each spot for prostaglandin $E_2$ and its decomposition products, i.e., prostaglandin $A_2$ and prostaglandin $B_2$ was measured by means of a recording type densitometer, COSMO Densitometer Chromato Ace D-109 type, to determine the peak area of each spot, and then the content of prostaglandin $E_2$ in the sample was calculated from the area ratio. The ratio of the content per ampoule of prostaglandin $E_2$ in each of the lyophilized products obtained in Examples 1-6 and stored at 35° C. for 30 days (and for further 90 days for the lyophilized product obtained in Example 1) to the initial content of prostaglandin $E_2$ per ampoule in the lyophilized products was calculated as the residual percentage. The results are shown in Table I.

Table I

| Sample | Residual percentage of prostaglandin $E_2$ when the lyophilized products were stored for 30 days at 35° C. |
|---|---|
| Example 1* | 94.4% |
| Example 2 | 100% |
| Example 3 | 90% |
| Example 4 | 80% |
| Example 5 | 100% |
| Example 6 | 100% |

*The residual percentate of prostaglandin $E_2$ in the lyophilized product obtained in Example 1 stored for further 90 days at 35° C. was 83.6%.

In addition, when the crystal of prostaglandin $E_2$ prepared without using the stabilizer of this invention was stored for 30 days at 35° C., the residual percentage was 10%.

Then, the stabilization effect of the stabilizers of this invention for each prostaglandin $E_2$ group was determined by measuring the residual percentage of the lyophilized formulations prepared according to the process of this invention when the formulations were stored for 16 days at 45° C. The results are shown in the following table.

Table II

| Prostaglandin $E_2$ (PGE$_2$) group | Stabilizer | Amount per vial | Residual percentage | Ex. No. |
|---|---|---|---|---|
| 16-Methyl-PGE$_2$ | Dextran 20 | 200 mg. | 95% | 7 |
|  | Dextran 70 | 60 mg. | 95% | 8 |
|  | mannitol (control) | 56 mg. | 70% |  |
|  | none | 0 | 60% |  |
| 3-Methyl-PGE$_2$ | Dextran 20 | 60 mg. | 100% | 9 |
|  | Manitol (control) | 56 mg. | 70% |  |
|  | none | 0 | 60% |  |
| 3,16(R)-Dimethyl-PGE$_2$* | Dextran 20 | 200 mg. | 100% | 10 |
|  | Polyvinyl pyrrolidone | 5 mg. | 90% | 12 |
|  | Mannitol (control) | 56 mg. | 70% |  |
|  | none | 0 | 60% |  |
| 17-Oxo-15-epi-PGE$_2$* | Dextrin | 50 mg. | 100% | 11 |
|  | Methyl cellulose | 5 mg. | 85% | 13 |
|  | Mannitol (control) | 56 mg. | 50% |  |
|  | none | 0 | 0 |  |
| 16(R)-Hydroxy-PGE$_2$* | Glutathione | 20 mg. | 95% | 14 |
|  | Oxidized glutathione | 20 mg. | 95% | 15 |
|  | Mannitol (control) | 56 mg. | 70% |  |
|  | none | 0 | 60% |  |

*novel compound

The invention will further be illustrated by the following examples.

EXAMPLE 1

A solution of 100 mgs. of prostaglandin $E_2$ in crystalline form in 1 ml. of ethanol was placed in a two-liter vessel to dampen the wall of the vessel with the solution and then the ethanol was removed by distilling under reduced pressure or by passing nitrogen gas therethrough. Then, 10 g. of methyl cellulose and 1800 ml. of distilled water were added to the residue to dissolve methyl cellulose and after adjusting the system to pH 6.5 by adding an aqueous solution of sodium hydroxide, the mixture was stirred to dissolve prostaglandin $E_2$. Then, distilled water was added to the solution to make the whole volume 2000 ml. The solution was then subjected to sterile filtration according to a conventional manner, filled in ampoules at 1 ml. per ampoule, and after subjecting each sample to lyophilization, the ampoule was sealed by fusing.

EXAMPLE 2

A solution of 100 mgs. of prostaglandin $E_2$ in crystalline form in 1 ml. of ethanol was placed in a two-liter vessel to dampen the wall of the vessel with the solution and then the ethanol was removed by distilling under reduced pressure or by passing nitrogen gas therethrough. Then, 30 g. of glutathione and 1900 ml. of distilled water were added to the residue to dissolve glutathione and after adjusting the pH thereof to 6.5 by adding an aqueous solution of sodium hydroxide, the mixture was stirred in a nitrogen gas stream to dissolve prostaglandin $E_2$. Then, distilled water was added to the solution to make the whole volume 2000 ml. After subjecting the solution to sterile filtration according to a conventional manner, the solution was filled in ampoules at 1 ml. per ampoule, and after subjecting it to lyophilization, the ampoule was sealed by fusing.

EXAMPLE 3

A solution of 100 mgs. containing prostaglandin $E_2$ in crystalline form in 1 ml. ethanol was placed in a two-liter vessel to dampen the wall of the vessel with the solution and then the ethanol was removed by distilling under reduced pressure or by passing nitrogen gas therethrough. Then, when 400 g. of dextran 20 having a mean molecular weight of 20,000 and 1200 ml. of distilled water was added to dissolve the dextran, the pH of the solution became about 6.5. After further stirring the mixture to dissolve prostaglandin $E_2$, distilled water was added to the solution thus formed to make the whole volume 2000 ml. Then, after subjecting the solution to sterile filtration according to a conventional manner, the solution was filled in ampoules at 1 ml. per ampoule and after lyophilizing the solution, the ampoule was sealed by fusing.

EXAMPLE 4

A solution of 100 mgs. of prostaglandin $E_2$ in crystalline form in 1 ml. of ethanol was placed in a two-liter vessel to dampen the wall of the vessel with the solution and then the ethanol was removed by distilling under a reduced pressure or by passing nitrogen gas therethrough. Then, 50 g. of gelatin and 1800 ml. of distilld water were added to the residue to dissolve gelatin and after adjusting the pH thereof to 6.5 by adding an aqueous solution of solium hydroxide, the mixture was stirred to dissolve prostaglandin $E_2$. Then, after subjecting the solution to sterile filtration according to a conventional manner, the solution was filled in ampoules at 1 ml. per ampoule and after lyophilizing the solution, the ampoule was sealed by fusing.

EXAMPLE 5

A solution of 100 mgs. of prostaglandin $E_2$ in crystalline form in 1 ml. of ethanol was placed in a two-liter vessel to dampen the wall of the vessel with the solution and then the ethanol was removed by distilling under reduced pressure of by passing nitrogen gas therethrough. Then, 60 g. of deoxycholic acid, 29.3 g. of arginine, and 1800 ml. of water were added to the residue to dissolve the arginine salt of deoxycholic acid thus formed in water and after adjusting the pH thereof to 7.0 by adding hydrochloric acid, the mixture was stirred to dissolve prostaglandin $E_2$. Then, distilled water was added to the solution to make the whole volume 2000 ml. After subjecting the solution to sterile filtration according to a conventional manner, the solution was filld in ampoules at 1 ml. per ampoule and after lyophilizing the solution, the ampoule was sealed by fusing.

EXAMPLE 6

A solution of 100 mgs. of prostaglandin $E_2$ in crystalline form in 1 ml. of ethanol was placed in a two-liter vessel to dampen the wall of the vessel with the solution and then the ethanol was removed by distilling under reduced pressure or by passing nitrogen gas therethrough. Thereafter, 60 g. of deoxycholic acid, 29.3 g. of arginine, and 1800 ml. of water were added to the residue to dissolve the arginine salt of deoxycholic acid formed in water and after adjusting the pH thereof to 8.5 by adding an aqueous solution of arginine, the mixture was stirred to dissolve prostaglandin $E_2$. Then, after subjecting the solution to sterile filtration, the solution ws filled in ampoules at 1 ml. per ampoule and after lyophilizing the solution, the ampoule was sealed by fusing.

EXAMPLE 7

A solution of 100 mgs. of 16-methyl-prostaglandin $E_2$ in crystalline form in 1 ml. of ethanol was placed in a two-liter vessel to dampen the wall of the vessel with the solution and then ethanol was removed by distilling under reduced pressure or by passing nitrogen gas therethrough.. Then, 400 g. of dextran 20 having a mean molecular weight of 20,000 and 1500 ml. of distilled water were added to the residue to dissolve the dextran and 16-methyl-prostaglandin $E_2$ and distilled water was added to the solution to make the whole volume 2000 ml. After subjecting the solution to sterile filtration according to a conventional manner, the solution was filled in vials at 1 ml. per vial and after lyophilizing the solution, the vial was sealed.

EXAMPLE 8

A solution of 100 mgs. of 16-methyl-prostaglandin $E_2$ in crystalline form in 1 ml. of ethanol was placed in a two-liter vessel to dampen the wall of the vessel with the solution and then ethanol was removed by distilling under reduced pressure or by passing nitrogen gas therethrough. Then, 120 g. of dextran 70 having a mean molecular weight of 70,000 and 1500 ml. of distilled water were added to the residue to dissolve the dextran and 16-methyl-prostaglandin $E_2$ in water and then distilled water was added to the solution to make the whole volume 2000 ml. Thereafter, the solution was subjected to sterile filtration according to a conventional manner, the solution was filled in vials at 1 ml. per vial, and after lyophilizing the solution, the vial was sealed.

EXAMPLE 9

A solution of 100 mgs. of 3-methyl-prostaglandin $E_2$ in crystalline form in 1 ml. of ethanol was placed in a two-liter vessel to dampen the wall of the vessel and then ethanol was removed by distilling under reduced pressure or by passing nitrogen gas therethrough. Then, 120 g. of dextran 20 having a mean molecular weight of 20,000 and 1500 ml. of distilled water were added to the residue to dissolve the dextran and 3-methyl-prostaglandin $E_2$ and then distilld water was added to the solution to make the whole volume 2000 ml. Then, after subjecting the solution to sterile filtration according to a conventional manner, the solution was filled in vials at 1 ml. per vial and after lyophilizing the solution, the vial was sealed.

EXAMPLE 10

A solution of 100 mgs. of 3,16(R)-dimethyl-prostaglandin $E_2$ in crystalline form in 1 ml. of ethanol was placed in a two-liter vessel to dampen the wall of the vessel and then ethanol was removed by distilling under reduced pressure or by passing nitrogen gas therethrough. Thereafter, 120 g. of dextran 20 having a mean molecular weight of 20,000 and 1500 ml. of distilled water were added to the residue to dissolve the dextran and 3,16(R)-dimethyl-prostaglandin $E_2$ and then distilled water was added to the solution to make the whole volume 2000 ml. Thereafter, after subjecting the solution to sterile filtration according to a conventional manner, the solution was placed in vials at 1 ml. per vial and after lyophilizing the solution, the vial was sealed.

EXAMPLE 11

A solution of 100 mgs. of 17-oxo-15-epi-prostaglandin $E_2$ in crystalline form in 1 ml. of ethanol was placed in a two-liter vessel to dampen the wall of the vessel and then ethanol was removed by distilling under reduced pressure or by passing nitrogen gas therethrough. Thereafter, 100 g. of dextrin and 1500 ml. of distilled water were added to the residue to dissolve the dextrin and then after adjusting the pH thereof to 6.5 by adding an aqueous solution of sodium hydroxide, the mixture was stirred to dissolve 17-oxo-15-epi-prostaglandin $E_2$. Then, distilled water was added to the solution to make the whole volume 2000 ml. Then, after subjecting the solution to sterile filtration according to a conventional manner, the solution was placed in vials at 1 ml. per vial and after lyophilizing the solution, the vial was sealed.

EXAMPLE 12

A solution of 100 mgs. of 3,16(R)-dimethyl-prostaglandin $E_2$ in crystalline form in 1 ml. of ethanol was placed in a two-liter vessel to dampen the wall of the vessel and then ethanol was removed by distilling under reduced pressure or by passing nitrogen gas therethrough. Then, 10 g. of polyvinyl pyrrolidone and 1500 ml. of distilled water were added to the residue to dissolve polyvinyl pyrrolidone and after adjusting the pH thereof to 6.5 by adding an aqueous solution of sodium hydroxide, the mixture was stirred to dissolve 3,16(R)-dimethyl-prostaglandin $E_2$. Thereafter, distilled water was added to the solution to make the whole volume 2000 ml. Then, after subjecting the solution to sterile filtration according to a conventional manner, the solution was placed in vials at 1 ml. per vial and after lyophilizing the solution, the vial was sealed.

EXAMPLE 13

A solution of 100 mgs. of 17-oxo-15-epi-prostaglandin $E_2$ in crystalline form in 1 ml. of ethanol was placed in a two-liter vessel to dampen the wall of the vessel and then ethanol was removed by distilling under reduced pressure or by passing nitrogen gas therethrough. Then, 10 g. of methyl cellulose and 1500 ml. of distilled water were added to the residue to dissolve methyl cellulose and after adjusting the pH thereof to 6.5 by adding an aqueous solution of sodium hydroxide, the mixture was stirred to dissolve 17-oxo15-epi-prostaglandin $E_2$. Thereafter, distilled water was added to the solution to make the whole volume 2000 ml. Then, after subjecting the solution to sterile filtration, the solution was filled in vials at 1 ml. per vial and after lyophilizing the solution, the vial was sealed.

EXAMPLE 14

A solution of 100 mgs. of 16(R)-hydroxy-prostaglandin $E_2$ in crystalline form in 1 ml. of ethanol was placed in a two-litter vessel to damp the wall of the vessel and then ethanol ws removed by distilling under reduced pressure or by passing nitrogen gas therethrough. Then, 40 g. of glutathione and 1500 ml. of distilled water were added to the residue to dissolve glutathione and after adjusting the pH thereof to 6.5 by adding an aqueous solution of sodium hydroxide, the mixture was stirred to dissolve 16(R)-hydroxy-prostaglandin $E_2$. Thereafter, distilled water was added to the solution to make the whole volume 2000 ml. Then, after subjecting the solution to sterile filtration according to a conventional manner, the solution was filled in vials at 1 ml. per vial and after lyophilizing the solution, the vial was sealed.

EXAMPLE 15

A solution of 100 mgs. of 16(R)-hydroxy-prostaglandin $E_2$ in crystalline form in 1 ml. of ethanol was placed in a two-liter vessel to dampen the wall of the vessel and then ethanol was removed by distilling under reduced pressure or by passing nitrogen gas therethrough. Then, 40 g. of oxidized glutathione and 1500 ml. of distilled water were added to the residue to dissolve exidized glutathione and after adjusting the pH thereof to 6.5 according to a conventional manner, the solution was filld in vials at 1 ml. per vial and after lyophilizing the solution, the vial was sealed.

We claim:

1. A process of preparing a stable prostaglandin E-containing formulation which comprises adding to prostaglandin $E_1$, $E_2$ or $E_3$ at least one member selected from the group consisting of an arginine salt, a lysine salt and an alkali metal salt of deoxycholic acid and subjecting the resulting mixture to lyophilization, said arginine salt, lysine salt or alkali metal salt of deoxycholic acid being present in an amount varying between 1 to 200 mg. per 0.05 mg. of said prostaglandin E.

2. A process as claimed in claim 1 wherein said prostaglandin E is a member selected from the group consisting of 16-methyl-prostaglandin $E_2$, 3-methyl-prostaglandin $E_2$. 3-16(R)-dimethyl-prostaglandin $E_2$, 17-oxo-15-epi-prostaglandin $E_2$, and 16(R)-hydroxy-prostaglandin $E_2$.

3. A process as claimed in claim 1 wherein when said prostaglandin E is in a crystalline state, the crystals are dissolved in an organic solvent followed by removal of the solvent before the additive is added to said prostaglandin E.

4. A process as claimed in claim 3 wherein said organic solvent is ethanol or ethyl acetate.

5. A process as claimed in claim 1 wherein said prostaglandin E is a natural prostaglandin E.

6. A process as claimed in claim 1 wherein said prostaglandin E is a synthetic prostaglandin E.

7. A process according to claim 1 in which 5–100 mgs. of said arginine salt, lysine salt and alkali metal salts of deoxycholic acid are added to 0.05 mg. of said prostaglandin E.

8. A lyophilized pharmaceutical composition comprising as the active ingredient a therapeutically effective amount of prostaglandin $E_1$, $E_2$ or $E_3$ and at least one member selected from the group consisting of an arginine salt, a lysine salt and alkali metal salts of deoxycholic acid, said arginine salt, lysine salt and alkali metal salts of deoxycholic acid being present in an amount from 1 to 200 mg. per 0.05 mg. of said prostaglandin E.

9. A lyophilized pharmaceutical composition as claimed in claim 8 wherein said prostaglandin E is a member selected from the group consisting of 16-methyl-prostaglandin $E_2$, 3-methyl-prostaglandin $E_2$, 3-16(R)-dimethyl-prostaglandin $E_2$, 17-oxo-15-epi-prostaglandin $E_2$, and 16(R)-hydroxy-prostaglandin $E_2$.

10. A lyophilized pharmaceutical composition as claimed in claim 8 wherein said prostaglandin E is a natural prostaglandin E.

11. A lyophilized pharmaceutical composition as claimed in claim 8 wherein said prostaglandin E is a synthetic prostaglandin E.

* * * * *

UNITED STATES PATENT OFFICE
CERTIFICATE OF CORRECTION

Patent No. 4,092,428    Dated May 30, 1978

Inventor(s) Masuo Murakami, et al

It is certified that error appears in the above-identified patent and that said Letters Patent are hereby corrected as shown below:

In the Abstract, line 5: "and a" should be --or a--.

Column 1, lines 25, 35 & 44, in the formulas: " \\\ " should be -- ⁄⁄⁄ --.

Column 1, lines 28, 37 & 47, in the formulas: " ≡ " should be -- ⋮ --.

Column 1, line 56: After "such" insert --various--.

Column 1, line 61: After "decomposed" cancel the semi-colon.

Column 2, line 36: "and a" should be --or a--.

Column 5, line 39: "of 100 mgs. containing" should be --containing 100 mgs.--.

Column 5, line 62: "distilld" should be --distilled--.

Column 5, line 65: "solium" should be --sodium--.

UNITED STATES PATENT OFFICE
CERTIFICATE OF CORRECTION

Patent No. 4,092,428      Dated May 30, 1978

Inventor(s) Masuo Murakami, et al

It is certified that error appears in the above-identified patent and that said Letters Patent are hereby corrected as shown below:

Column 8, line 14: "oxo15" should be --oxo-15--.

Column 8, line 45: "exidized" should be --oxidized--.

Signed and Sealed this

Twenty-ninth Day of May 1979

[SEAL]

Attest:

RUTH C. MASON
*Attesting Officer*

DONALD W. BANNER
*Commissioner of Patents and Trademarks*